(12) United States Patent
Dietz et al.

(10) Patent No.: US 11,986,375 B2
(45) Date of Patent: *May 21, 2024

(54) INFLATABLE EARPLUG SYSTEM

(71) Applicant: CREARE LLC, Hanover, NH (US)

(72) Inventors: Anthony Dietz, Phoenix, AZ (US);
Marc C. Ramsey, Meriden, NH (US)

(73) Assignee: CREARE LLC, Hanover, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/223,007

(22) Filed: Jul. 17, 2023

(65) Prior Publication Data

US 2023/0363952 A1    Nov. 16, 2023

Related U.S. Application Data

(63) Continuation of application No. 17/576,941, filed on Jan. 15, 2022, now Pat. No. 11,723,807.

(60) Provisional application No. 63/138,433, filed on Jan. 16, 2021.

(51) Int. Cl.
*A61F 11/10*    (2006.01)
(52) U.S. Cl.
CPC .................................. *A61F 11/10* (2013.01)
(58) Field of Classification Search
CPC .............................. A61F 11/10; A61F 11/085
See application file for complete search history.

(56) References Cited

U.S. PATENT DOCUMENTS

| | | | | |
|---|---|---|---|---|
| 2,535,258 A * | 12/1950 | Bland | ................... | H04R 25/656 128/865 |
| 2,876,767 A * | 3/1959 | Wasserman | ............. | A61F 11/10 128/865 |
| 3,110,356 A * | 11/1963 | Mendelson | ............. | A61F 11/10 128/865 |
| 3,505,999 A * | 4/1970 | Harvey | ................... | A61F 11/10 128/865 |
| 3,783,864 A * | 1/1974 | Moller | ................. | H04R 25/656 128/864 |
| 3,799,170 A * | 3/1974 | Walsh | ................... | A61M 29/02 606/193 |

(Continued)

*Primary Examiner* — Camtu T Nguyen
(74) *Attorney, Agent, or Firm* — Skaar Ulbrich Macari, P.A.

(57) ABSTRACT

A deep insert, inflatable hearing protection earplug is provided that is easy for an untrained user to insert correctly, reliably providing high acoustic attenuation and remaining both secure and comfortable for long durations in a human ear. The earplug comprises a soft elastomer shell that forms a sealed volume filled with an inert fluid. The earplug can comprise a slender, flexible stem that is easily insertable into the ear canal when deflated. The proximal end of the earplug can be situated outside the ear canal, within the concha of the ear, and incorporates a bulb with a hemispherical, bistable cap. After inserting the shaft of the earplug into the ear canal, the wearer applies force with a finger to invert the cap, which transitions elastically from a convex to a concave external geometry, displacing a fixed volume of fluid to inflate a sheath that forms the outer covering of the stem, filling and sealing the ear canal. The sheath can be deflated by pulling on or otherwise engaging a release tab or other feature attached to the cap.

21 Claims, 3 Drawing Sheets

(56) References Cited

U.S. PATENT DOCUMENTS

| | | | | |
|---|---|---|---|---|
| 4,006,796 | A * | 2/1977 | Coehorst | H04R 25/656 |
| | | | | 128/865 |
| 4,060,080 | A * | 11/1977 | Akiyama | A61F 11/10 |
| | | | | 128/865 |
| 4,133,984 | A * | 1/1979 | Akiyama | H04R 25/456 |
| | | | | 381/381 |
| 4,834,211 | A * | 5/1989 | Bibby | H04R 25/656 |
| | | | | 381/328 |
| 4,896,679 | A * | 1/1990 | St. Pierre | A61F 11/10 |
| | | | | 128/868 |
| 4,913,165 | A * | 4/1990 | Fishgoyt | A61F 11/10 |
| | | | | 128/865 |
| 5,483,027 | A * | 1/1996 | Krause | A61F 11/10 |
| | | | | 128/865 |
| 6,094,494 | A * | 7/2000 | Haroldson | H04R 25/652 |
| | | | | 381/328 |
| 6,256,396 | B1 * | 7/2001 | Cushman | H04R 25/652 |
| | | | | 381/328 |
| 7,227,968 | B2 * | 6/2007 | van Halteren | H04R 25/656 |
| | | | | 381/328 |
| 7,779,844 | B2 * | 8/2010 | Purcell | A61F 11/10 |
| | | | | 128/865 |
| 8,550,206 | B2 * | 10/2013 | Keady | A61F 11/08 |
| | | | | 181/135 |
| 9,138,353 | B2 * | 9/2015 | Keady | A61M 25/10181 |
| 11,723,807 | B2 * | 8/2023 | Dietz | A61F 11/10 |
| | | | | 128/865 |
| 2009/0173353 | A1 * | 7/2009 | Purcell | A61F 11/10 |
| | | | | 128/865 |
| 2009/0320859 | A1 * | 12/2009 | Purcell | A61F 11/10 |
| | | | | 128/864 |
| 2022/0226157 | A1 * | 7/2022 | Dietz | A61F 11/10 |

\* cited by examiner

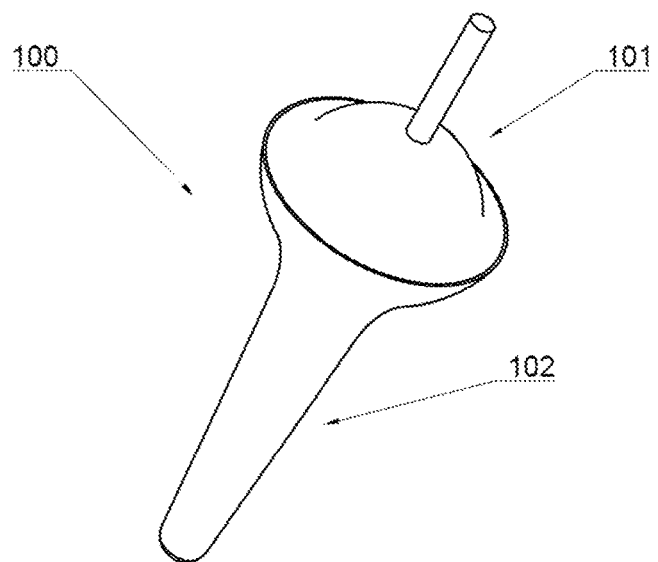
FIG. 1
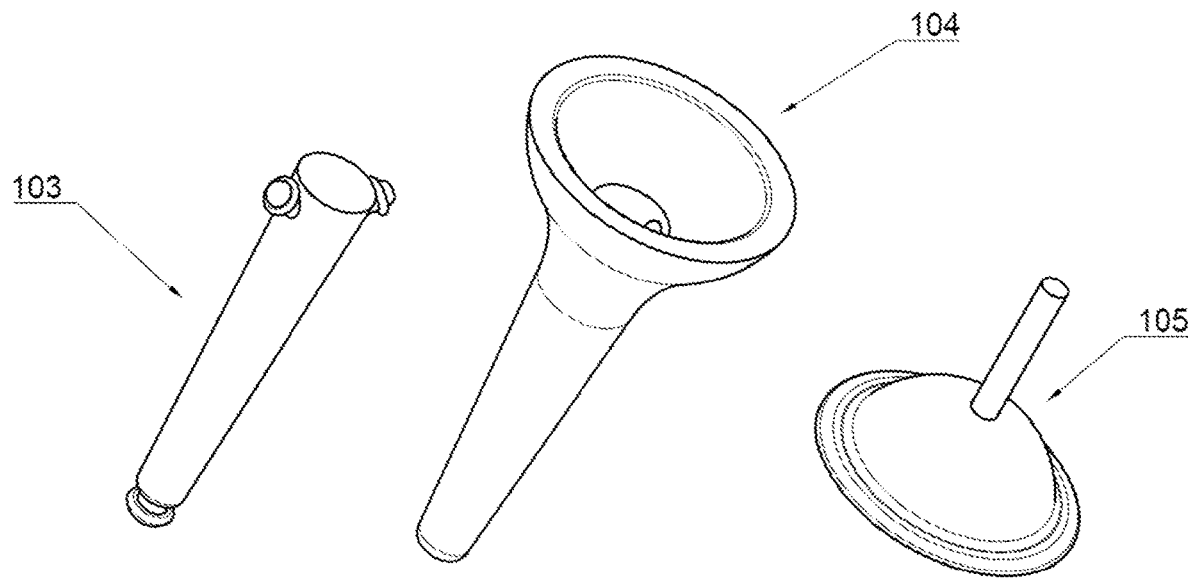
FIG. 2A　　FIG. 2B　　FIG. 2C the sheath that forms the outer covering of the stem, filling and sealing the ear canal. The sheath can be deflated by pulling on or otherwise engaging a release tab or other feature attached to the cap.

INFLATABLE EARPLUG SYSTEM

CROSS-REFERENCE TO RELATED APPLICATIONS

The present application is a continuation of U.S. patent application Ser. No. 17/576,941, filed Jan. 15, 2022, which claims priority to and the benefit of U.S. Provisional Patent Application No. 63/138,433, filed Jan. 16, 2021; with each of the referenced applications and disclosures fully incorporated herein by reference.

FIELD

The present invention relates generally to hearing protection devices and, more particularly, to an inflatable earplug system and device that is comfortable and easy for an untrained user to fit and remove, and which produces a high-attenuation acoustic seal deep in the ear canal.

BACKGROUND

Hearing protection is needed by those engaged in occupations or activities involving loud intermittent or sustained noise. Insufficient protection in loud noise environments can lead to permanent hearing damage with related hearing loss or tinnitus. Hearing damage negatively affects communication, job performance, and quality of life, and results in increased health care costs.

There are many earplugs and earmuffs on the market that attempt to reduce or eliminate the potential damage noisy environments can have on the human ear. Conventionally, high levels of noise attenuation require large earmuffs, which are bulky, and can be uncomfortable to wear, or deeply inserted earplugs, which can be difficult and painful to insert properly. Poorly fitted devices that do not seal to the head or in the ear canal at sufficient depth provides low levels of attenuation, leaving the user at risk of hearing damage. If a hearing protection device is not easy to fit correctly and comfortable, it will not be used or, if used, it will not be effective.

As a result, there is a need for a new and improved earplug system and device that solves the innate functional and design flaws of conventional configurations, designs, and approaches.

SUMMARY

Embodiments of the present invention include an earplug system and device that forms a high-attenuating acoustic seal deep in the ear canal, is comfortable, easy for an untrained user to fit and use, intrinsically adaptable to the broad variety of human ear canal anatomies, and secure for long term wear in active environments, while still being easily removable when desired. The earplug device provides a reliable acoustic seal past the second bend of the ear canal, which will ensure high attenuation.

The earplug comprises a soft elastomer shell that forms a sealed volume filled with an inert fluid. The earplug can comprise a slender, flexible stem that is easily insertable into the ear canal when deflated. The proximal end of the earplug can be situated outside the ear canal, within the concha of the ear, and incorporates a bulb with a hemispherical, bistable cap. After inserting the stem of the earplug into the ear canal, the wearer applies force with a finger to invert the cap, which transitions elastically from a convex to a concave external geometry, displacing a fixed volume of fluid to inflate a Another object of the invention is to provide such an acoustic seal that optionally incorporates an internal air channel for desirable pass-through acoustics. Various filters may be inserted in this channel to affect the frequency-dependent and level-dependent attenuation of the earplug.

Another object of the invention is to provide an earplug device that creates such a seal but is readily manufacturable and durable for many uses over extended periods of time, leading to low overall costs.

The slender stem with a soft, fluid-filled, elastic sheath enables a user to easily insert deep into the ear canal and then inflate manually. The sheath expands, conforming to the inner profile of the ear canal, and produces an acoustic seal with large surface area at uniform pressure. The constant-pressure conformability of the sheath provides a comfortable and uniform seal deep in the ear canal without pressure points that can cause discomfort. Further, the large contact surface of the area securely anchors the earplug within the ear.

The high acoustic impedance of the fluid that fills the sheath relative to air results in low transmission of ambient sound. The central stabilizing core constrains the inflation of the sheath in the axial direction, ensuring radial inflation, and damps axial oscillation of the fluid volume that might otherwise allow transmission of low frequency sound. The core also provides for the possibility to incorporate the internal pass-through acoustic channel.

Attached to the distal end of the sheath, the bistable hemispherical bulb forms a sealed volume filled with fluid. The bulb provides a reservoir for the fluid when the sheath is deflated. The bulb is an elastomeric hemisphere that is mechanically stable in either a concave or convex topology. When the bulb is inverted by force from the user's finger, a fixed volume of fluid is displaced and forced into the sheath. The geometry and material of the bulb are selected to provide the appropriate displaced volume for inflation of the sheath, and to retain the required inflation pressure without inadvertent inversion. The bulb can also incorporate a tab as an integrally molded component. To remove the earplug, the user grasps the tab and pulls, first inverting the bulb to release the inflation pressure, then continuing to extract the deflated earplug from the ear.

The geometry of the sheath is tailored to provide advantageous inflation behavior. The sheath is thinnest near its tip, ensuring that the onset of inflation and sealing occurs deep in the ear. The wall thickness of the sheath is tapered, increasing toward the bulb and outer ear. Inflation initiated at the tip will progress gradually outward toward the bulb with steadily increasing pressure as fluid is transferred from the bulb into the sheath. This allows ear canals of various sizes to be accommodated with a single earplug design. Large diameter ear canals will seal with greater radial expansion at the tip of the sheath and a shorter inflated region and seal in the axial direction. Small diameter ear canals will seal with less radial expansion and a longer or larger inflated region progressing axially along the stem toward the outer ear. The sheath is sufficiently thick, or very thick, in the concave region adjacent to the bulb to ensure that this portion does not inflate.

The above summary is not intended to describe each illustrated embodiment, claimed embodiment or implementation of the invention. The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the spirit and scope of the present invention.

BRIEF DESCRIPTION OF THE DRAWINGS

The invention may be more completely understood in consideration of the following detailed description of various embodiments of the invention in connection with the accompanying drawings, in which:

FIG. 1 shows an isometric view of an inflatable earplug system or device in a nominal state prior to insertion, in accordance with embodiments of the present invention.

FIG. 2A shows an isometric view of a core of an inflatable earplug system or device, in accordance with embodiments of the present invention.

FIG. 2B shows an isometric view of a sheath of an inflatable earplug system or device, in accordance with embodiments of the present invention.

FIG. 2C shows an isometric view of a bi-stable cap of an inflatable earplug system or device, in accordance with embodiments of the present invention.

Figure 3A:
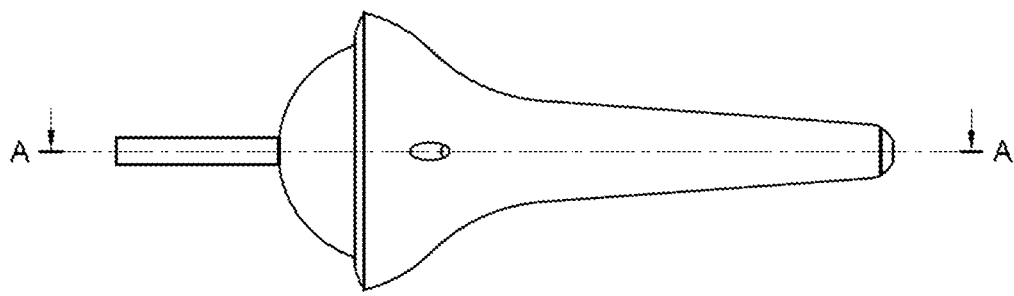
FIG. 3A shows an orthographic view of an inflatable earplug system or device in the same nominal state as FIG. 1, in accordance with embodiments of the present invention.

While the invention is amenable to various modifications and alternative forms, specifics thereof have been shown by way of example in the drawings, are not intended to be to scale, and will be described in detail. It should be understood, however, that the intention is not to limit the invention to the particular embodiments described. On the contrary, the invention is to cover all modifications, equivalents, and alternatives falling within the spirit and scope of the invention as defined by the appended claims.

DETAILED DESCRIPTION

The system and device of the present invention, shown in FIG. 1, is an inflatable hearing protection earplug 100 comprising a stem 102 that is inserted into a user's ear canal and a bulb 101 that protrudes from their ear canal. The length of the stem 102 should be commensurate with the typical depth of the human ear canal, typically in the range of 0.5-1.0 inches. It may be advantageous to provide multiple (e.g., two or three) different standard sizes of earplugs with different stem lengths to accommodate different ear sizes.

In various preferred embodiments, the earplug 100 components or parts are made of molded silicone materials. Silicones are chemically inert, bio-compatible, durable, elastic, resilient, easily molded to intricate shapes by several different processes, readily bonded together permanently with silicone adhesives, and available in a variety of formulations with a large range of durometer hardness, elongation, and other critical mechanical properties. Particular silicone formulations are selected with mechanical properties beneficial to the function of each specific component or part. It should be understood that alternative embodiments might employ other elastomeric materials, including but not limited to urethanes, nitriles, or latex rubber.

Referring to FIGS. 2A-2C, the earplug 100 is assembled from three primary components or parts: a core 103, a sheath 104, and a bi-stable cap 105.

Figure 3B:
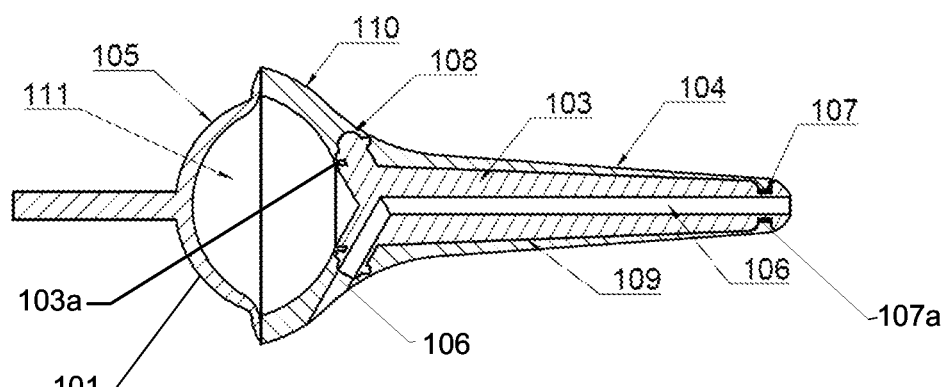
FIG. 3B shows a detail section view of the inflatable earplug system or device along cross-section A-A of FIG. 3A, in accordance with embodiments of the present invention.

The method by which these components are assembled to form the stem 102 and the bulb 101 is evident in the section views of FIGS. 3A-3B—e.g., showing the earplug 100 in a deflated state with a fluid 111 stored in the volume of the bulb 101. The sheath 104 is in operative fluid communication with the fluid volume 111 in the bulb 101 via one or more channels, transmission paths or like features between the sheath 104 and the core 103 at the interface 103a, as shown in FIG. 3B. The stem 102 is formed by overmolding or otherwise assembling the sheath 104 onto the core 103. During use, the sheath 104 inflates to seal the ear canal. The functions of the core 103 are: to give the stem 102 stiffness while deflated and being inserted into the ear canal; to constrain the axial extension of the sheath 104 into the ear canal as it is inflated, preventing pain or damage to the eardrum; to damp axial motion of the inflated sheath that otherwise might transmit low frequency sound; and, optionally, to provide the isolated air channel 106 for pass-through sound.

The sheath 104 is fixed to the core 103 at either end using adhesive and possibly anchoring features such as those shown at the tip or end portion 107 of the core 103 to prevent leakage, and at the base 108 to prevent axial elongation. The sheath 104 is free to separate from the core surface 109 between these features when inflated. The core 103 includes an o-ring type groove 107a to improve adhesion at the tip 107. The anchors 108 include a ridge or groove for the same reason. In preferred embodiments, this adhesion is achieved through silicone-on-silicone bonding while overmolding the sheath 104 onto the core 103 or through adhesive if otherwise assembled.

The core 103 is made of a silicone with intermediate durometer hardness, giving it flexibility for insertion, but enough stiffness to resist extension under inflation and dynamic pressures and to resist collapse of the acoustic channel when the earplug is inflated. In various preferred embodiments, the core 103 is constructed of a silicone rubber with durometer hardness of 40 on the Shore A scale.

The material of the sheath 104 should have very low durometer hardness and high elongation, allowing it to inflate like a balloon and strain several hundred percent at low pressure, preferably below 2 pounds per square inch (PSI). In a preferred embodiment, the sheath 104 is constructed of a silicone rubber with durometer hardness of 10 on the Shore A scale and elongation at break in excess of 400%.

The bulb 101 serves to seal the predefined fluid volume and provide a mechanism for displacing fluid to inflate the sheath 104. In various preferred embodiments, the bulb 101 incorporates a bistable hemispherical cap 105 for the latter function and assumes a convex shape before inflation of the earplug 100. The bulb 101 is formed by adhering the bi-stable cap 105 to the outer face of the sheath's flange 110. The sealed volume within the bulb 101 formed by the cap 105 and the sheath 104 is filled with unpressurized fluid 111, which may be air, water, oil, or other fluids. It will be understood by one skilled in the art that various other designs, materials, and constructions could achieve the same objectives consistent with the disclosure provided herein. The bulb 101 or cap 105 can include a diaphragm, one or more bellows, a valve, or a pump to facilitate fluid displacement.

In use, the narrow stem 102 of the deflated earplug is inserted into a user's ear until the flange 110 is seated against the ear canal opening, providing a fixed and repeatable insertion depth. The user then presses the bi-stable cap 105, forcing fluid 111 from the bulb 101 into the sheath 104 until the cap 105 is inverted or otherwise defines a concave shape (or approaches an inverted or concave shape) and the sheath 104 is inflated.

Figure 4A:
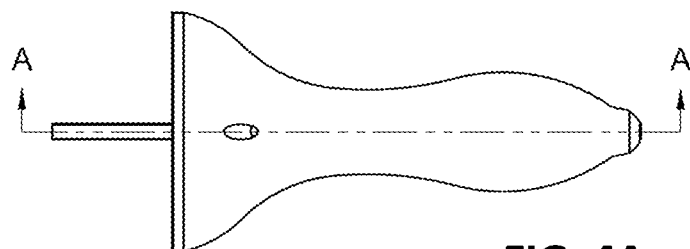
FIG. 4A shows an orthographic view of an inflatable earplug system or device in an inflated state, in accordance with embodiments of the present invention.
Figure 4B:
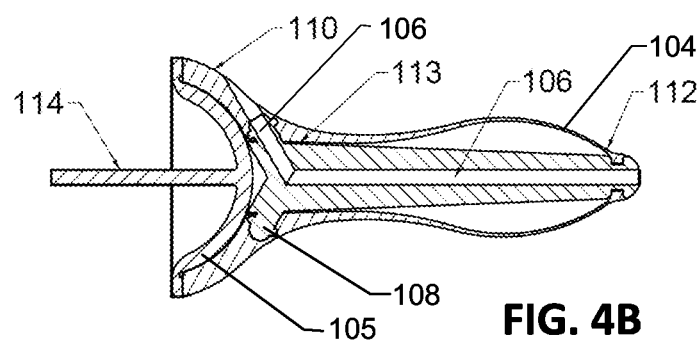
FIG. 4B shows a detail section view of the inflatable earplug system or device along cross-section A-A of FIG. 4A, in accordance with embodiments of the present invention.

Referring to FIGS. 4A-4B, section views of the earplug 100 in an inflated state are shown. The thickness of the sheath 104 varies from thinnest at the earplug tip or end portion 112 to thickest at the flange 110. Pressurized fluid 111 squeezed from the bulb 101 will pass through channels or unsealed transmission paths between the sheath 104 and the core 103 or will otherwise separate the sheath 104 from the core 103, creating an interstitial space 113 through which the fluid 111 will flow until it reaches the tip 112, where the sheath 104 is thinnest and where it will first inflate. This important aspect of the design ensures the earplug 100 will first create a seal at the tip 112, which is located in the deepest portion of the ear canal.

As the sheath 104 at the tip 112 expands in the radial direction, the increased pressure required for further expansion will begin to inflate the increasingly thicker sheath 104 away from the tip 112, and the inflated region will grow in the axial direction toward the flange 110. As a result, air is forced out of the ear canal, rather than inward, as the earplug sheath 104 inflates. This action prevents pressurization of the sealed portion of the ear canal, which could otherwise create an unbalanced pressure force against the ear drum, causing pain.

When the earplug 100 is inflated in an ear canal, radial expansion at the tip 112 is constrained by the canal walls and a seal is formed. Further inflation will then increase the seal contact area. Thus, tapering of the sheath 104 thickness ensures the earplug 100 will create an effective seal in ear canals of varying diameter. In wide ear canals, the radius of the inflated sheath 104 at the tip 112 will be larger and the axial length of the inflated region will be less than in narrow ear canals, which will have a smaller inflation radius and longer axial region of inflation to accommodate the same volume of inflation fluid. To keep inflation pressure low and provide good conformability to the ear canal, the wall thickness of the sheath 104 near the tip 112 must be very thin, preferably in the range of 0.002-0.006 inches. The thickness of the sheath 104 at the flange 110 should be greater, preferably in the range of 0.010-0.050 inches.

An acoustic channel 106 through the core 103 and the flange 110 provides a pass-through by which sounds may be introduced past the earplug seal. Various filters may be inserted in this channel to affect the frequency-dependent and level-dependent attenuation of the earplug.

To withdraw the earplug 100, the user pulls on the release tab 114 to pop the cap 105 into its original convex or non-inverted form. This action will suck fluid 111 back into the bulb 101 and deflate the sheath 104. The earplug 100 may then be pulled from the user's ear canal.

Figure 5:
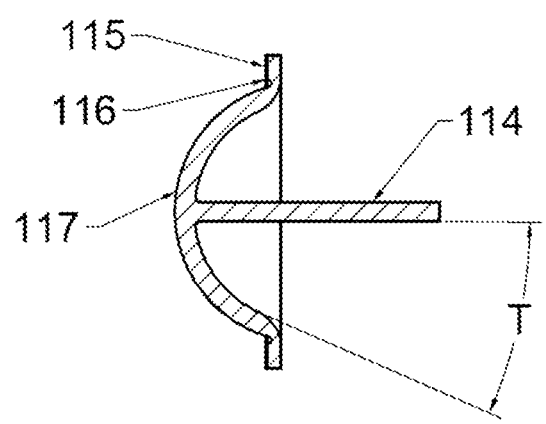
FIG. 5 shows a detail section view of a cap of an inflatable earplug system or device, in accordance with embodiments of the present invention.

Referring to FIG. 5, the bi-stable cap 105 provides a simple and easy-to-use mechanism and methodology for the user to inflate the sheath 104 and ensure that it remains inflated during use. The cap 105 is defined by geometric features for various preferred embodiments, including a flat land 115 for adhering to the flange 110, a thin elastic hinge region 116 to enable inversion, and a hemispherical region 117 of uniform thickness. The cap 105 is preferably molded as a single component in its externally convex configuration and including the release tab 114. The angle T between the tab 114 and an end portion of the hemispherical region 117 is important to the bistable function and operation of the cap 105 and is predefined appropriately, with a preferred value in the range of 20-30 degrees.

The cap 105 geometry is carefully tuned to achieve elastic stability in both concave and convex topologies, preferably with maximal stability in the concave case in order to resist the inflation pressure and avoid inadvertent release during use. In the preferred embodiment, the cap 105 resists between 2 and 3 PSI in that position. To achieve this performance, the cap 105 is preferably constructed of a relatively stiff silicone with durometer hardness of 60 on the Shore A scale. This silicone should also have high elongation capability to enable resilience and durability in the elastic hinge region 116. The inversion displacement of the cap 105 is matched to the sheath inflation volume required to achieve a good seal in the ear canal. In various preferred embodiments, the inversion displacement of the cap 105 is in the range of 0.025-0.050 cubic inches. In certain embodiments, it may be advantageous to provide multiple (e.g., two or three) different standard sizes of earplugs 100 with different displacement volumes to accommodate various ear sizes.

For a highly attenuating earplug 100, it is desirable for the earplug inflation fluid 111 to have acoustic impedance (the product of density and sound speed) which differs significantly from that of air. Most common liquids meet this requirement.

It is also beneficial to select a liquid with low vapor pressure. All silicones have high permeability, and the liquid tends to diffuse through the silicone sheath 104. A liquid with higher vapor pressure (such as water) tends to evaporate from the outer surface of the sheath 104. This evaporation maintains a concentration gradient across the sheath 104, driving further diffusion and ultimately depleting the volume of liquid contained in the earplug 100 over time. A liquid with low vapor pressure will still diffuse through the sheath 104 but will not evaporate when reaching the outer surface. This brings diffusion to a halt and prevents significant depletion of the liquid volume. This diffusive process also maintains a thin layer of liquid on the exterior of the sheath 104, providing a slight lubrication effect which can be beneficial to the function and comfort of the earplug.

Further, it is important for the fluid 111 to be inert and biocompatible. It should be safe for contact with the ear canal as a result of diffusion, or in the case of a leak or rupture of the sheath 104. In certain preferred embodiments, these requirements are met with liquids such as glycerol, mineral oil, or silicone oil. In alternative embodiments, other liquids might also be used.

In another embodiment, the earplug fluid 111 may be a gas instead of a liquid. Experimental data show that such a gas-filled earplug provides modest sound attenuation, but a very flat frequency response. This may be beneficial for some applications. For example, musicians are chronically exposed to high sound levels during performance and would benefit from some level of hearing protection, without sacrificing acoustic fidelity.

In the various preferred embodiments of the invention, the three elastomer components of the earplug 100, e.g., the core 103, the sheath 104, and the bi-stable cap 105, are fabricated efficiently by molding using two-part liquid silicone, heat cured liquid silicone, or heat cured high consistency silicone rubber. The core 103 is molded first, then the sheath 104 is over-molded onto the core 103. This overmolding process naturally forms the required mechanical attachment and seal at the tip 107 of the sheath 104 and the anchor points 108. The required release between the sheath 104 and the core 103 at the tapered interface 109 is achieved by applying a mold release agent to that surface of the stem 102 prior to the overmolding process. These steps will be readily understood by one skilled in the art of molding.

Alternatively, the sheath 104 may be formed separately from the core 103 by a process such as injection molding or dip molding and may then be assembled onto the core with adhesive being applied to seal the tip 107 and anchor the base 108.

The cap 105 can be formed separately by simple injection molding. It is then permanently adhered to the open end of the sheath 104 with an appropriate adhesive.

The fluid 111 can be introduced into the sealed volume after the cap 105 is adhered by injection with a hypodermic needle through the thick, spherical portion of the sheath 104. Any gas bubbles remaining in the sealed volume can be extracted with the same hypodermic needle after the correct volume of liquid has been injected. When the sheath 104 is made of a soft silicone material and the hypodermic needle is small gauge and sharp, and the injection site is substantially self-sealing and does not result in a leak after the needle is removed. Alternatively, the fluid 111 may be introduced before the cap 105 is adhered by using an external vacuum to inflate the sheath 104 at the stem 102. The fluid 111 will fill the inflated region 104 and the cap 105 may be adhered in its concave form. Other methods are also possible.

The present invention may be embodied in other specific forms without departing from the spirit or essential attributes thereof, and it is, therefore, desired that the present embodiment be considered in all respects as illustrative and not restrictive. Similarly, the above-described methods and techniques for providing and using the present invention are illustrative processes and are not intended to limit the methods of manufacturing the present invention to those specifically defined herein. Further, features and aspects of the various embodiments described herein can be combined to form additional embodiments within the scope of the invention even if such combination is not specifically described herein.

What is claimed is:

1. An inflatable earplug device, comprising:
an expandable sheath including a proximal portion in fluid communication with a distal portion; and
a bistable element including an elastic hinge region connected to the proximal portion of the expandable sheath to form a fluid-fillable cavity, wherein the bistable element is configured to invert into the fluid-fillable cavity from a first shape to a second shape to displace fluid from the fluid-fillable cavity to inflate the distal portion of the expandable sheath to facilitate an acoustic ear canal seal.

2. The device of claim 1, wherein the expandable sheath includes an elastomer material to facilitate inflatable expansion.

3. The device of claim 2, wherein the elastomer material expands at pressure below two Pounds per Square Inch (PSI).

4. The device of claim 1, wherein the expandable sheath includes a wall having a tapered thickness.

5. The device of claim 4, wherein the tapered thickness of the wall increases from the distal inflatable end portion to the proximal end portion of the expandable sheath.

6. The device of claim 1, further including a core element connected to the distal portion to facilitate controlled inflation of the expandable sheath.

7. The device of claim 6, wherein the core element includes one or more air channels to facilitate pass-through sound.

8. The device of claim 1, wherein the fluid has an acoustic impedance different than air.

9. The device of claim 1, wherein the fluid includes at least one of: a glycerol, a mineral oil, a silicone oil, or a gas.

10. The device of claim 1, wherein the expandable sheath includes a flange to facilitate seating.

11. The device of claim 1, wherein the bistable element is manually manipulated to displace the fluid.

12. The device of claim 1, wherein the bistable element includes a diaphragm.

13. The device of claim 1, wherein the bistable element is a bistable hemispherical bulb element.

14. The device of claim 1, wherein a geometry of the bistable element is configured to resist at least 2 PSI of inflation pressure.

15. The device of claim 1, wherein the bistable element includes a release tab to release inflation pressure.

16. The device of claim 1, wherein the expandable sheath is constructed of a low durometer elastomer and the bistable element is constructed of a high durometer elastomer.

17. An inflatable earplug device, comprising:
an expandable sheath constructed of an elastomer and includes a proximal portion in fluid communication with an inflatable portion such that a tapered wall thickness of the expandable sheath increases from the inflatable portion to the proximal portion; and
a bistable cap including an elastic hinge region connected to the proximal portion of the expandable sheath to form a fluid-fillable cavity, wherein the bistable cap is configured to invert to displace fluid from the fluid-fillable cavity to inflate the expandable sheath to facilitate an acoustic ear canal seal.

18. The device of claim 17, further including a core element anchored to the expandable sheath to facilitate controlled inflation of the expandable sheath.

19. The device of claim 18, wherein the core element includes one or more air channels to facilitate pass-through sound displacement.

20. The device of claim 17, wherein the bistable cap is hemispherical and is constructed of a high durometer elastomer, and the expandable sheath is constructed of a low durometer elastomer.

21. The device of claim 17, wherein the bistable cap includes a release tab to release inflation pressure.

* * * * *